United States Patent [19]

Arndt et al.

[11] Patent Number: 4,824,962

[45] Date of Patent: Apr. 25, 1989

[54] PROCESS FOR THE PREPARATION OF NAPHTHOSTYRIL

[75] Inventors: Otto Arndt, Hofheim am Taunus; Theodor Papenfuhs, Frankfurt, am Main, both of Fed. Rep. of Germany

[73] Assignee: Hoechst Aktiengesellschaft, Frankfurt am Main, Fed. Rep. of Germany

[21] Appl. No.: 170,065

[22] Filed: Mar. 14, 1988

Related U.S. Application Data

[63] Continuation of Ser. No. 914,485, Oct. 2, 1986, abandoned.

[30] Foreign Application Priority Data

Oct. 4, 1985 [DE] Fed. Rep. of Germany ....... 3535482

[51] Int. Cl.$^4$ ............................................ C07D 209/92
[52] U.S. Cl. .................................................. 548/437
[58] Field of Search ........................................ 548/437

[56] References Cited

FOREIGN PATENT DOCUMENTS 2237372 2/1974 Fed. Rep. of Germany .
55-35051 3/1980 Japan .

OTHER PUBLICATIONS

Chem. Abs., Number Section, 1965–71, Registry Nos. 26500-00-5 through 30299-99-1, No. 29878-91-9.
Ullmanns Encyklopaedie deo technischen Chemie, 4th Ed., vol. 9, Verlag Chemie, 1975, pp. 543–44.

*Primary Examiner*—Mary E. Ceperley

[57] ABSTRACT

Process for the preparation of naphthostyril by dissolving 1,8-naphthalimide in an aqueous solution of lithium hydroxide and potassium hydroxide while heating at 40° C. to 80° C., cooling the solution obtained to 14° C. and seeding it at said temperature with a maximum of 1 mol-% of sodium 1,8-naphthalimide per 1 mol of 1,8-naphthalimide used, then adding chlorine bleaching liquor at 10° C. to 20° C., reductively removing excess active chlorine after the reaction has taken place, adjusting the alkaline aqueous solution produced of the alkali-metal salt of the 1-aminonaphthal-ene-8-carboxylic acid formed to a pH of 2.0 by adding acid and isolating the naphthostyril which precipitates in this process.

5 Claims, No Drawings

PROCESS FOR THE PREPARATION OF NAPHTHOSTYRIL

This is a continuation of application Ser. No. 914,485 filed Oct. 2, 1986, now abandoned.

The subject of the invention is a process for the preparation of naphthostyril which has been improved compared with the prior art.

From the Japanese Published Patent Application Sho-58-45 425 (Preliminary Published Japanese Patent Application Sho-55-35 051) a process is known for preparing naphthostyril of the formula

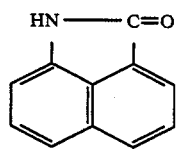

in which an alkaline aqueous solution of 1,8-naphthalimide, prepared by means of sodium hydroxide, potassium hydroxide or preferably a mixture thereof at above 40° C., is cooled to 15° C. until the naphthalimide at least partially crystallizes and is then reacted with hypochlorite in the form of chlorine bleaching liquor at 20° C. In this process the Na:K quantity ratio is a maximum of 0.9 and a minimum of 0.25. The optimum reaction time is specified as 2½ hours. The yield is said to be 83%. The disadvantage of this method is in the use of a vary large quantity of hypochlorite (3–5 mol per mol of 1,8-naphthalimide) which leads to the resinification and formation of naphthalic acid anhydride.

From Khimiya i khimicheskaya tekhnologiya 4 (1961), 2, 232-237 it is known that too high excesses of hypochlorite lead to resinification which impairs the quality of the product, for example as a result of specks, but, as in-house investigations have shown, this cannot be detected from the melting point.

Copying the exemplary embodiment quoted in the said Japanese patent application did not result in the yield of 83% quoted there, but of only 58%, the product obtained having an net content of 76% (according to HPLC (High Performance Liquid Chromatography) and being permeated with dark specks. The low naphthalimide content of the product (1%) indicates a virtually complete reaction.

Copying the exemplary embodiment of the said Japanese patent application is of importance insofar as in said example no quality data of any kind, such as melting point, net content, subsidiary components, are quoted for the naphthostyril obtained.

According to the procedure described in the Russian Literature reference quoted, the parameters which determine the yield of naphthostyril, i.e. concentration, temperature, reaction time, excess of alkali (NaOH, KOH) and excess of hypochlorite (NaOCl+NaCl) are optimized. However, the procedure described therein differs from the procedure of the said Japanese application in that the reaction is said to proceed at high dilution (12 liters of water per mol of naphthalimide) and with large excess of alkali-meal hydroxide (NaOH+KOH=12 mol per mol of naphthalimide), which opens up the possibility of using less hypochlorite (1.9 mol per mol of naphthalimide). The optimum reaction time is specified as 2½ hours. The yield is said to be 85-90%. The melting point is specified as 174°-178° C. The only other quality information is the nitrogen content (7.83%-8.06%) (theoretical: 8.28%). The high dilution means, however, a small space-time yield and the high excess of alkali leads to a severe waste-water load due to inorganic salts, as a result of which the known process under discussion is uneconomical and causes environmental pollution.

It has now been found that naphthostyril can be prepared in an advantageous manner while avoiding the drawbacks besetting the said processes by modifying the process known from the cited Japanese patent application in a manner such that the 1,8-naphthalimide is dissolved in an aqueous solution of lithium hydroxide and potassium hydroxide instead of in an aqueous solution of sodium hydroxide and/or potassium hydroxide and the solution of naphthalimide obtained is seeded with a maximum of 1 mol-% of crystalline sodium 1,8-naphthalimide per 1 mol of dissolved naphthalimide at 14° C.

The subject of the invention is therefore a process for the preparation of naphthostyril which comprises dissolving 1,8-naphthalimide in an aqueous solution of lithium hydroxide and potassium hydroxide while heating at 40° C. to 100° C., preferably 45° C. to 80° C., cooling the solution obtained to 14° C. and seeding it at said temperature with a maximum of 1 mol-% of crystalline sodium 1,8-naphthalimide per 1 mol of dissolved naphthalimide, then adding chlorine bleaching liquor at 10° C. to 20° C., preferably 14° to 16° C., after the reaction has taken place reductively removing excess active chlorine, expediently by adding an aqueous alkali metal bisulfite solution, then adjusting the alkaline aqueous solution which has been obtained of the 1-aminonaphthalene-8-carboxylic acid formed to pH 2.5, preferably 2.0, by adding an acid, for example a mineral acid such as hydrochloric acid, and isolating the naphthostyril which precipitates in this process.

The chlorine bleaching liquor used is to be understood as an equivalent mixture of sodium hypochlorite and sodium chloride as described in Gmelins Handbuch der Anorganischen Chemie (Gmelin's Handbook of Inorganic Chemistry) 6, 8th edition (1927), page 293 or Ullmanns Enzyklopadie der Technischen Chemie 9, 4th edition (1975), page 544.

The advantages of the process according to the invention over the said known processes are that (1) the naphthostyril is produced in better quality, i.e. with a higher degree of purity of 92–95% and, in addition, is speckfree (2) because of the small quantity of hypochlorite to be used, less sulfite is required to destroy the excess active chlorine, as a result of which a reduction in the sulfate and chloride loading of the waste water is provided, and (3) in spite of the use of less hypochlorite, the optimum reaction time of 2½ hours can be maintained.

The crystalline sodium 1,8-naphthalimide used for seeding is prepared from 1,8-naphthalimide and sodium hydroxide solution.

The crystallization of the sodium salt of 1,8-naphthalimide (after previous seeding of the alkaline aqueous solution of 1,8-naphthalimide) while chlorine bleaching liquor is being run in ensures a constant and adequately low concentration of the dissolved sodium 1,8-naphthalimide during the reaction, which is of great importance for a reproducible control of the reaction.

If crystallization of the dissolved sodium 1,8-naphthalimide is prevented by not seeding (prevention of the formation of crystallization nuclei), the reaction, which otherwise proceeds in the heterogeneous phase (the sodium 1,8-naphthalimide is present as a precipitate), proceeds in solution. The consequence is a substantial reduction of the yield.

In the process according to the invention the quantity and concentration of hypochlorite can be considerably reduced, the concentration by at least 25%. Said reduction of the concentration and quantity of hypochlorite is made possible by the use of lithium hydroxide instead of sodium hydroxide when dissolving the 1,8-naphthalimide (preparation of the "imide liquor").

It must therefore be considered surprising that the considerable reduction of the hypochlorite concentration and quantity, despite the remarks in the Japanese patent cited, does not lead to a lengthening of the reaction time and an impairment of the quality associated therewith, but to a marked improvement of the quality of the naphthostyril with the reaction time remaining constant and optimum.

If the procedure is as described above according to the invention, but with the modification that the 1,8-naphthalimide is dissolved in an aqueous solution of sodium hydroxide and potassium hydroxide instead of in an aqueous solution of lithium hydroxide and potassium hydroxide (preparation of the "imide liquor"), the advantages described above and provided over the process of the Japanese patent application cited are retained. However, under these conditions the optimum reaction time is lengthened from 2½ to 4½ hours.

Further details and preferred embodiments of the process according to the invention are specified below.

Expediently, an approximately 4 percent by weight aqueous solution of lithium hydroxide and potassium hydroxide or sodium hydroxide and potassium hydroxide is prepared, the LiOH:KOH molar ratio expediently being 1:1.5, or the NaOH:KOH molar ratio expediently being such that of a total of 3 mol of alkali-metal hydroxide a maximum of 2 mol are KOH. An expedient NaOH:KOH molar ratio is, for example, 1.2:1.8.

According to the reaction scheme

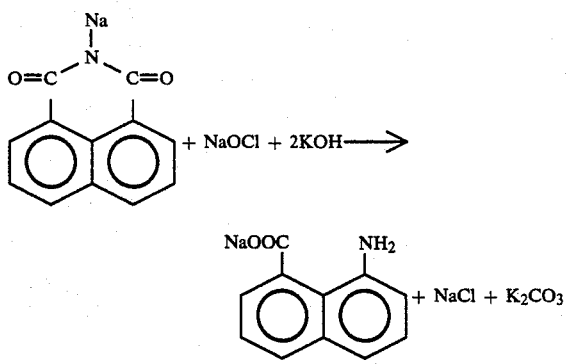

3 mol of alkali-metal hydroxide, including the alkali-metal hydroxide quantity required for forming the alkali-metal salt of 1,8-naphthalimide, are required for the course of the reaction (Hofmann degradation), 2 mol thereof for the neutralization of the carbonic acid eventually formed. 1,8-Naphthalimide is dissolved at approximately 80° C. in the alkaline aqueous solution prepared as a moist or dry product with a minimum net content of 90%. When it is completely dissolved, the solution is cooled to 14° C., no crystallization occurring. Defoaming agent and dispersant are then added to the solution. The solution thus obtained is the "imide liquor".

A crystal slurry of sodium naphthalimide is then prepared, expediently by dissolving 2 g of 1,8-naphthalimide in 50 ml of hot water at 80° C. containing 2 g of 100% sodium hydroxide and grinding the mixture to form a crystalline slurry at 20° C. This slurry is added to the "imide liquor". Apart from the seeded crystals added, no crystallization should occur as yet. Immediately thereafter 2.3 mol of a 13–13.5% chlorine bleaching solution (water content: 940 g) is allowed to run in in the course of 2 minutes while stirring. In total the mixture therefore contains 6400 g of water to 200 g of naphthalimide (32:1). The crystallization should already commence while the chlorine bleaching liquor is being run in or immediately thereafter.

After the chlorine bleaching liquor has been run in, the temperature should rise to 18° C. in 5 minutes. Stirring of the reaction mixture is then continued at 18° C. for 2½ hours. After approximately 1½–2 hours the precipitate has disappeared.

Even slight changes in the parameters mentioned may have substantial effects on yield and quality.

The water used should be within the limits of 5–6 liters per 1 mol of 1,8-naphthalimide, the upper limit being non-critical.

The quantity of alkali-metal hydroxide should be between 5–6 mol per 1 mol of 1,8-naphthalimide; quantities which are too low or too high are harmful. Instead of the lithium hydroxide, sodium hydroxide can be used in the variant of the process. The duration of the reaction is in this case 4½ hours (the crystalline precipitate disappears after approximately 4 hours).

The temperature in the post stirring stage should be between 16° C. and 20° C. Below 16° C. the reaction proceeds only very slowly, above 20° C. resinification occurs to an increasing extent.

The addition of a defoaming agent is to be recommended to avoid any accumulation of explosive nitrogen trichloride and to be able to exploit the capacity of the vessel better.

The dispersant is intended to provide for a uniform crystal growth.

The titer of the chlorine bleaching liquor must be tested shortly before it is used. It should be stored at 5° C. and used at 10° C.

The establishment of the starting temperature of 14° C. in the "imide liquor" is important. It is matched to the heat capacity of the reaction mixture. This is intended ensure that the reaction mixture reaches the temperature level of 18° C., which is ideal for the reaction, as soon as possible (after approximately 5 minutes) after the chlorine bleaching liquor is run in. The post-stirring time (if lithium hydroxide is used) of 2½ hours should be maintained as accurately as possible. A post-stirring time of at least 2 to at most 3 hours if lithium hydroxide is used represents the extreme limits of the duration of the post-treatment. Even time intervals of 30 minutes can produce marked effects:

After 2 hours naphthalimide is still clearly detectable, after 3 hours the resinification reactions (which can be detected by the increasing discoloration of the reaction solution from bright orange to dark reddish brown) start. The optimum post-stirring times also depend on the quality of the 1,8-naphthalimide used. Because of the reaction of dissolved subsidiary components, 90% 1,8-naphthalimide consumes hypochlorite more quickly than 100% 1,8-naphthalimide, as a result of which the reaction rate of the target reaction is slowed down (by approximately 30 minutes). If LiOH is replaced by NaOH, the optimum post-stirring time is 4½ hours.

At the end of post-stirring time, the excess chlorine present as Cl+ has to be eliminated by reduction with sulfite to chloride Cl−. In this process 1 mol of Cl+ consumes 1 mol of $SO_3^{2-}$. The end point of the destruction of the excess active chlorine is detected by dabbing onto potassium iodide starch paper. It emerges that if approximately 100% 1,8-naphthalimide is used a further 0.72 mol of sulfide is required, but if approximately 90% 1,8-naphthalimide is used only 0.36 mol of sulfite. The different quantity (or concentration) of hypochlorite of approximately 20% corresponding to said difference of the quantities of sulfite required manifests itself in a difference of about 30 minutes of post-stirring time. After the destruction of the active chlorine, the procedure is essentially in accordance with the procedure of the Japanese patent application cited.

The reaction solution is then heated to 90° C. and the pH is adjusted to 2.0 with approximately 5.9 mol of 30% hydrochloric acid, in which process precipitation commences from pH 4.5 according to the reaction equation

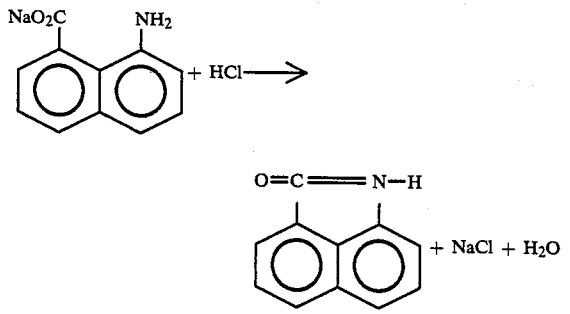

Precipitations commencing at pH>4.5 indicate a large quantity of naphthalimide.

Stirring of the weakly acid solution is continued at 90° C. for 1 hour and a 15% soda solution is added to adjust the pH to 8.5 (consumption approximately 0.9–1.2 mol of soda), as a result of which that portion of the resins is dissolved which was not present previously as specks. Products which contain specks as a result of too much hypochlorite being used are not freed of these specks by this so-called "soda extraction".

0.73 mol (corresponding to a yield of 73% of theory) of naphthostyril is obtained having a net content of 92% (HPLC), a content of a maximum of 2% of 1,8-naphthalimide and a maximum of 2% of naphthalic acid anhydride. The melting point is 173° C.–176° C.

Naphthostyril (1,8-naphtholactam (CAS (Chemical Abstracts)) No. [130-00-7]) is an important starting product for the preparation of 1,1'-dinaphthyl-8,8'-dicarboxylic acid (CAS No. [29878-91-9]) and an important intermediate product for the preparation of acid dyestuffs and dispersed dyestuffs and also of cationic dyestuffs, in particular polyacrylonitrile and polyester dyestuffs. The use of naphthostyril is described, for example, in the German Offenlegungsschriften No. 2,237,372, 2,309,612, 2,341,657, 2,036,504 and 1,931,789, and also in the German Auslegeschrift No. 1,917,456, German Pat. No. 1,444,660 and German Pat. No. 1,225,326.

The process according to the invention is explained by the examples below without being limited thereto.

EXAMPLE 1

A solution of 50 g of lithium hydroxide 1-hydrate 55% (1.13 mol of LiOH) and 107 g of potassium hydroxide 89% (1.70 mol) in flake form in 3000 ml of water is prepared in a 6 liter flask with stirrer. 108 g of naphthalimide as a water-moist product (net content of the dry product at least 98%=0.547 mol) is completely dissolved in said solution at 80° C. The solution is cooled to 14° C. and 170 mg of a defoaming agent (fluorinated organic compound) and 170 mg of a dispersant (specific organic polyelectrolyte) are added. A crystal slurry of sodium naphthalimide (prepared from 1.08 g of 1,8-naphthalimide+30 ml of water+2.50 ml of 33% NaOH) is added to the clear solution of the "imide liquor" obtained at 14° C. The total amount of 1,8-naphthalimide used is 109.1 g (0.553 mol).

680 g of 13% chlorine bleaching liquor (1.245 mol of active chlorine, corresponding to 2.26 mol of active chlorine/mol of imide), which is adjusted to 10° C., is allowed to run in to the "imide liquor" seeded in this manner in the course of 2 minutes with vigorous stirring.

During, or at the latest at the end of, the running in of the chlorine bleaching liquor crystalline precipitation begins and the temperature rises to 16° to 18° C. Stirring is continued at 18° C. After approximately 85 minutes the crystalline precipitate has disappeared. Stirring is continued for 2½ hours in total (calculated from the start of the running in of the chlorine bleaching liquor). The excess of active chlorine (Cl+) is then destroyed by running in 102 g of a 40% aqueous sodium hydrogensulfite solution (0.39 mol) at 18° C. In addition a further 14 g is added as excess. The solution is heated to 90° C. and stirring is continued at 90° C. for ½ hour (pH 10.6). 381 g of 315 hydrochloric acid (3.24 mol HCl) are then allowed to run in at 90° C. in the course of 15 minutes until the pH is 2.0. The solution must be clear until the pH is 4.5. Precipitation sets in from pH 4.5. At pH 2.0 a pale, olive green suspension is present which must not contain any specks. Stirring is continued for 1 hour at 90° C. and 463 g of 15% soda solution (0.65 mol) is then added at 80° C. until the pH is 8.5 and stirring is continued for ½ hour at 80° C.

A yellow suspension is obtained which contains no specks. The suspension is then cooled to 25° C. and filtered through a nutsch filter using vacuum. Washing is then carried out with 400 ml of water until the discharge is colorless. 68.5 g of naphthostyril are obtained as a moist product (corresponding to 73% of theory). The net content of the dry product (74 g) is 92 to 95%. The powder has a pale yellow appearance.

The melting point is 173° C. to 176° C. The following may be mentioned as impurities: 0.8% 1,8-naphthalimide and 1.8% 1,8-naphthalic acid anhydride. In addition approximately 2–4% of chloronaphthostyril are also present. A precipitate of 16 g of a solid, which proves to be heavily contaminated naphthalic acid anhydride (content approximately 70%), is obtained at pH 2.0 from the waste water using hydrochloric acid. A further 3% of the material used are therefore missing from the material balance and remain in the waste water but can be biologically degraded therein.

EXAMPLE 2

The procedure is as described in Example 1, but with the modification that, instead of lithium hydroxide, sodium hydroxide is used (137 g of 33% sodium hydroxide solution (1.17 mol)). In this case the precipitation of the sodium 1,8-naphthalimide commences immediately after the seeding of the "imide liquor". After the running in of the chlorine bleaching liquor has been completed, stirring is continued for 4½ hours at 18° C. The crystalline precipitate disappears after approximately 3½-4 hours. 89 g of 40% sodium hydrogensulfite solution (0.34 mol) are required to destroy the excess of active chlorine. 393 g of 31% hydrochloric acid are required to precipitate the naphthostyril. 463 g of 15% soda solution are required for the soda extraction. Yield and quality of the naphthostyril obtained are identical with those of Example 1.

EXAMPLE 3

The procedure is as described in Example 1, but a 1,8-naphthalimide is used which was prepared by a dry route from 1,8-naphthalic acid anhydride and gaseous ammonia and is therefore heavily contaminated. The net content is only 90%.

After running in the chlorine bleaching liquor, stirring is continued for 2½ hours at 18° C. The crystalline precipitate disappears after approximately 100 minutes. 68 g of 40% sodium hydrogensulfite solution (0.26 mol) are required to destroy the excess of active chlorine, 381 g of 31% hydrochloric acid for the precipitation of naphthostyril and 347 g of 15% soda solution for the soda extraction.

Yield and quality of the naphthostyril obtained coincide with those of Example 1.

EXAMPLE 4

The procedure is as described in Example 1, but with the difference that after running in the chlorine bleaching liquor stirring is continued only for 2 hours at 18° C. 116 g of 40% sodium hydrogensulfite solution (0.45 mol) are required to destroy the excess of active chlorine. As in example 1, 74 g of naphthostyril is obtained after drying at 110° C. Although the net content (96.0%) is higher, and consequently also the yield (76% of theory), the product still contains perceptibly more naphthalimide (2.2%) than the product obtained according to Example 1 (0.8%). The content of anhydride is 1.8%.

EXAMPLE 5

The procedure is as described in Example 1, but with the difference that only 1.5 liters of water are taken for the "imide liquor". Even at 80° C. the imide is present as a suspension. Despite this, here too, as is usual in accordance with the invention, seeding is carried out at 14° C. and chlorine bleaching liquor is added. After 5 hours at 18° C. a suspension is present which, according to the external appearance, is still unchanged. 259 g of 40% of sodium hydrogensulfite solution (1.0 mol) are required to destroy the active chlorine. As a modification to the working up specified in Example 1, the precipitate is then immediately filtered. 57 g of contaminated naphthalimide (content approximately 90%) are retained.

EXAMPLE 6

The procedure is as described in Example 1, but with the following modifications:
(1) A well cleaned apparatus which is free of seeding nuclei is used.
(2) A naphthalimide of the same quality as in Example 3 is used.
(3) No seeding is carried out.
(4) Stirring is continued only for 2 hours at 18° C.

After the running in of the chlorine bleaching liquor has been completed, no precipitation commences. The more powerful evolution of heat at the beginning of the reaction indicates a higher rate of reaction. 61 g of 40% sodium hydrogensulfite solution (0.24 mol) are required to destroy the excess of active chlorine, 381 g of 31% hydrochloric acid to precipitate the naphthostyril and 347 g of 15% soda solution for the soda extraction. The suspension contains no specks.

The yield of naphthostyril is only 62.4 g (100% strength). Dry product 68 g. Net content=91.8% (HPLC).

The contaminants are: 1.4% naphthalimide, 1.9% naphthalic acid anhydride (HPLC). Melting point 172°-174° C. The loss in yield is brought about by an increased proportion of soda-soluble resin products.

EXAMPLE 7

(comparison example according to Japanese Preliminary Published Specification Sho-55-35 051, portions of Example 1 of the present invention which are not subject to claim being adapted)

A solution of 111 g of 33% sodium hydroxide solution (0.91 mol) and 58 g of 89% purity potassium hydroxide (0.91 mol) in flake form is made up in 2160 ml of water in a 6 liter flask with stirrer. 108 g of 1,8-naphthalimide as a water-moist product (net content of the dry product at least 98%) (0.547 mol) are completely dissolved in this solution at 70° C. The solution is cooled to 14° C. and stirred at said temperature until crystals form (approximately ½ hour). No seeding takes place.

897 g of 13% chlorine bleaching liquor (1.642 mol of active chlorine, corresponding to 3.0 mol of active chlorine per mol of imide), which is adjusted to 10° C., is allowed to run into the "imide liquor" prepared in this manner in the course of 2 minutes with vigorous stirring. At the same time a cold solution (temperature of the solution : 20° C.) of 100 g of 33% sodium hydroxide solution (0.82 mol) in 790 ml of water is run in. Toward the end of the running in a white crystalline precipitation commences abruptly. The suspension foams vigorously. Stirring is continued at 18°-19° C. until solution occurs, for which purpose 2¾ hours are needed. The excess of active chlorine is then destroyed by running in 150 g of 40% sodium hydrogensulfite solution (0.58 mol) at 18° C. In addition, a further 14 g is added as excess. The solution is heated to 90° C. and stirring is continued for ½ hour at 90° C. (pH 10.7). 313 g of 31% hydrochloric acid (2.65 mol of HCl) are then allowed to run in at 90° C. in the course of 15 minutes until the pH is 2.0. Until a pH of approximately 5 the solution is clear. From pH 4.5 precipitation sets in. At pH 2.0 a yellow suspension permeated with dark specks is present. Stirring is continued for 1 hour at 90° C. and 463 g of 15% soda solution (0.65 mol) is then added at 80° C. until the pH is 8.5 and stirring is continued for ½ hour at 80° C. A dark brown suspension is obtained. The suspension is cooled to 25° C. and filtered through a nutch filter using vacuum. Washing is carried out with 400 ml of water until the discharge is colorless. 54.0 g of naphthostyril is obtained as a moist product (58% of theory). The product has a dark appearance. The net content of the dry product (=71.3 g) is 76%. The melting point is 160° C. to 162° C.

The following contaminants are present: 1,8-Naphthalimide (1%) and naphthalic acid anhydride (14.8%)

In HPLC up to approximately 4% of an unknown compound was additionally found.

We claim:

1. A process for the preparation of naphthostyril which comprises:

dissolving 1,8-naphthalimide in an aqueous solution of a combination of alkali metal hydroxides consisting essentially of (1) potassium hydroxide and (b) lithium hydroxide, the quantity of the combination of alkali metal hydroxides thereby applied being about 5 to about 6 moles per mole of 1,8-naphthalimide, the dissolving being carried out while heating to 40° to 80° C.;

cooling the resulting alkali metal 1,8-naphthalimide solution to 14° C. and seeding it at said temperature with a seeding amount, not exceeding 1 mol-% per mole of 1,8-naphthalimide used, of sodium 1,8-naphthalimide seed crystals, while substantially maintaining the alkali metal 1,8-naphthalimide in solution, except for said seed crystals;

adding chlorine bleaching liquor to the thus-seeded solution at 10° to 20° C. and commencing crystallization after the addition of the chlorine bleaching liquor has begun;

maintaining said reaction mixture at a temperature of 16° to 20° C. after the addition of the chlorine bleaching liquor has been completed, said reaction mixture now containing an alkaline aqueous solution of alkali metal salt of 1-aminonaphthalene-8-carboxylic acid, and removing excess active chlorine and adjusting the pH of said alkaline aqueous solution to below about 2.5 to form precipitated naphthostyril, and isolating the naphthostyril.

2. The process according to claim 1, wherein the LiOH:KOH molar ratio in the aqueous solution is 1:1.5.

3. A process according to claim 1, wherein 1,8-naphthalimide is dissolved in a 4% aqueous solution of the combination of alkali metal hydroxides.

4. A process according to claim 3, wherein the LiOH:KOH molar ratio in the aqueous solution is 1:1.5.

5. A process for the preparation of naphthostyril which comprises:

dissolving 1,8-naphthalimide in an aqueous solution of a combination of alkali metal hydroxides comprising (a) potassium hydroxide and (b) lithium or sodium hydroxide, the quantity of the combination of alkali metal hydroxides thereby applied being about 5 to about 6 mole per mole of 1,8-naphthalimide, the dissolving being carried out while heating to 40° to 80° C.;

cooling the resulting alkali metal 1,8-naphthalimide solution to 14° C. and seeding it at said temperature with a seeding amount, not exceeding 1 mol-% per mole of 1,8-naphthalimide used, of sodium 1,8-naphthalimide seed crystals, while substantially maintaining the alkali metal 1,8-naphthalimide in solution, except for said seed crystals;

adding chlorine bleaching liquor to the thus-seeded solution at 10 to 20° C. and commencing crystallization after the addition of the chlorine bleaching liquor has begun;

maintaining said reaction mixture at a temperature of 16° to 20° C. after the addition of the chlorine bleaching liquor has been completed, said reaction mixture now containing an alkaline aqueous solution of alkali metal salt of 1-aminonaphthalene-8-carboxylic acid, and removing excess active chlorine and adjusting the pH of said alkaline aqueous solution to below about 2.5 to form precipitated naphthostyril, and isolating the naphthostyril.

* * * * *

UNITED STATES PATENT AND TRADEMARK OFFICE
CERTIFICATE OF CORRECTION

PATENT NO. : 4,824,962
DATED : April 25, 1989
INVENTOR(S) : Otto Arndt and Theodor Papenfuhs It is certified that error appears in the above-identified patent and that said Letters Patent is hereby corrected as shown below:

Column 1, line 31: "vary" should be --very--.

Column 6, line 36: "315" should read --31%--.

Column 8, line 50: "313" should read --312--.

In claim 1, column 9, line 8: "(1)" should read --(a)--.

In claim 2, column 9, line 36: "The process" should read --A process--.

Signed and Sealed this

Seventeenth Day of July, 1990

Attest:

HARRY F. MANBECK, JR.

*Attesting Officer*  *Commissioner of Patents and Trademarks*